(12) United States Patent
Homoto et al.

(10) Patent No.: US 7,390,917 B2
(45) Date of Patent: Jun. 24, 2008

(54) METHOD FOR PRODUCING MIXTURE OF FLUOROALKYL IODIDE TELOMERS AND METHOD FOR PRODUCING MIXTURE OF FLUORINE-CONTAINING (METH)ACRYLATE ESTERS

(75) Inventors: Yukio Homoto, Osaka (JP); Kunitada Tanaka, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 538 days.

(21) Appl. No.: 11/074,707

(22) Filed: Mar. 9, 2005

(65) Prior Publication Data

US 2005/0148790 A1    Jul. 7, 2005

Related U.S. Application Data

(62) Division of application No. 10/466,869, filed as application No. PCT/JP02/00910 on Feb. 5, 2002, now Pat. No. 7,038,095.

(30) Foreign Application Priority Data

Feb. 7, 2001    (JP) ............... 2001-030848

(51) Int. Cl.
  *C07C 69/52*    (2006.01)
(52) U.S. Cl. ..................................... 560/223
(58) Field of Classification Search .............. 560/223
  See application file for complete search history.

(56) References Cited

U.S. PATENT DOCUMENTS

| | | | |
|---|---|---|---|
| 3,226,449 A | 12/1965 | Blanchard et al. | |
| 3,234,294 A | 2/1966 | Parsons et al. | |
| 3,404,189 A | 10/1968 | Blochl et al. | |
| 3,916,009 A | * 10/1975 | Jager | ................ 560/197 |
| 5,068,471 A | 11/1991 | Paul et al. | |
| 5,268,516 A | 12/1993 | Bertocchio et al. | |
| 5,639,923 A | 6/1997 | Von Werner | |
| 5,650,545 A | 7/1997 | Bertocchio et al. | |

FOREIGN PATENT DOCUMENTS

| | | |
|---|---|---|
| EP | 811594 A1 | 12/1997 |
| GB | 1189576 | 4/1970 |
| GB | 1256818 | 12/1971 |
| GB | 1535408 | 12/1978 |
| JP | 48-42852 B1 | 12/1973 |
| JP | 60-22687 B2 | 6/1985 |
| JP | 6-206908 A | 7/1994 |
| JP | 6-305995 A | 11/1994 |
| JP | 7-59525 B2 | 6/1995 |

* cited by examiner

*Primary Examiner*—Paul A Zucker
(74) *Attorney, Agent, or Firm*—Birch, Stewart, Kolasch & Birch, LLP

(57) ABSTRACT

A method of producing a mixture of fluorine-containing (meth)acrylate esters, the method including:
  (A) a telomerization step of obtaining the mixture of the fluoroalkyl iodide telomers;
  (B) an ethylene addition step of adding ethylene to the mixture of the fluoroalkyl iodide telomers obtained in the step (A) to give a mixture of ethylene adducts; and
  (C) an esterification step of reacting the mixture of the ethylene adducts obtained in the step (B) with a (meth)acrylate compound to obtain fluorine-containing (meth)acrylate esters.

4 Claims, 2 Drawing Sheets

METHOD FOR PRODUCING MIXTURE OF FLUOROALKYL IODIDE TELOMERS AND METHOD FOR PRODUCING MIXTURE OF FLUORINE-CONTAINING (METH)ACRYLATE ESTERS

This application is a Divisional of application Ser. No. 10/466,869, filed on Jul. 18, 2003, now U.S. Pat. No. 7,038,095, which claims priority of International Application PCT/JP02/00910 filed on Feb. 5, 2002 under the Patent Cooperation Treaty and Japanese Application No. 2001-030848 filed in Japan on Feb. 7, 2001, the entire contents of which are hereby incorporated by reference and for which priority is claimed under 35 U.S.C. § 120.

TECHNICAL FIELD

This invention relates to a method for producing a mixture of fluoroalkyl iodide telomers, and a method for producing a mixture of fluorine-containing (meth)acrylate esters wherein the mixture of the fluoroalkyl iodide telomers obtained according to the former method is used.

BACKGROUND ART

Telomerization is a reaction wherein a taxogen (X) is added to a telogen (AB) by application of heat or light under a suitable catalyst so that a polymer of low polymerization degree represented by the formula: $A(X)_m B$ (wherein m is generally in the range of 1 to 20), that is, a telomer is obtained. An example of telomerization known in the art is a reaction wherein a fluoroalkyl iodide is used as the telogen and tetrafluoroethylene is used as a taxogen and another fluoroalkyl iodide having the molecular weight higher than the telogen is obtained. This reaction can be regarded as a reaction for obtaining a tetrafluoroethylene adduct compound by adding tetrafluoroethylene to the telogen. Various methods utilizing this reaction for obtaining the industrially useful fluoroalkyl iodide have been proposed. Hereinafter, several examples of the methods are recited. It should be noted that in order to discriminate a fluoroalkyl iodide as a product from another fluoroalkyl iodide as a starting material, the former is referred to as a "fluoroalkyl iodide telomer."

U.S. Pat. No. 3,226,449 discloses a method for producing a perfluoroalkyl iodide telomer by means of a telomerization wherein tetrafluoroethylene is added to a perfluoroalkyl iodide using an organic peroxide as an initiator. The telomerization is carried out in a single step in a single reactor.

GB Patent 1,256,818, Japanese Patent Publication (Kokoku) No. 60-22687 (1985), U.S. Pat. No. 3,234,294, U.S. Pat. No. 3,404,189 and GB Patent 1,189,576 disclose a method for initiating a telomerization which is employed upon producing a perfluoroalkyl iodide telomer.

Japanese Patent Laid-Open (Kokai) Publication No. 6-206908 (1994), Japanese Patent Laid-Open (Kokai) Publication No. 6-305995 (1994), and Japanese Patent Publication (Kokoku) 7-59525 (1995) explain that the number of carbon atoms (or molecular weight) of a perfluoroalkyl iodide telomer needs to be in a specific range, and disclose methods for producing a perfluoroalkyl iodide telomer having the desired number of carbon atoms by means of telomerization degree is controlled by employing a specific procedure and a reactor having a specific shape.

DISCLOSURE OF INVENTION

Japanese Patent Laid-Open (Kokai) Publication No. 6-206908 (1994) and so on disclose methods for producing a perfluoroalkyl iodide telomer having the desired number of carbon atoms by controlling the telomerization reaction. However, the methods described in these documents present a problem of lacking in operation simplicity because they require to use a reactor having a specific shape and to circulate a portion of a reaction mixture at a specific position of the reactor. Further, since the reaction proceeds in a vapor phase in the methods described in these documents, the reaction temperature needs to be higher than a temperature at which the reaction proceeds in a liquid phase, which makes the methods disadvantage from the viewpoint of energy.

A first object of the present invention is to provide a method for producing a mixture of fluoroalkyl iodide telomers having polymerization degrees equal to or more than a desired one, by carrying out a simple operation without taking a lot of energy. A particular important object of the present invention is to provide a method for producing a mixture of telomers $C_2F_5(CF_2CF_2)_nI$ (wherein n is an integer denoting a polymerization degree), which consists of telomers having the polymerization degree n of 3 or more (specifically $C_8F_{17}I$ (n=3), $C_{10}F_{21}I$ (n=4), $C_{12}F_{25}I$ (n=5), $C_{14}F_{29}I$ (n=6) and so on) and preferably contains $C_8F_{17}I$ (n=3) in a largest amount, by means of telomerization wherein $C_2F_5I$ is a telogen and tetrafluoroethylene (which may be referred to as "TFE" in this specification) is a taxogen.

A second object of the invention is to provide a method for producing a mixture of fluorine-containing (meth)acrylate esters each of which has an alkoxyl group whose number of carbon atoms is equal to or more than a predetermined value by using the mixture of the fluoroalkyl iodide telomers produced in accordance with the method described above. The number of carbon atoms of the fluorine-containing (met) acrylate ester depends on the polymerization degree n of the fluoroalkyl iodide telomer. A particular important object of the present invention is to provide a method for producing a mixture of fluorine-containing (meth)acrylate esters represented by the formula $C_2F_5(CF_2CF_2)_n CH_2CH_2OCOCR^1=CH_2$ (wherein $R^1$ is hydrogen or a methyl group) so that each ester has n of 3 or more, and preferably so that $C_8F_{17}CH_2CH_2OCOCR^1=CH_2$ (n=3) is contained in a largest amount in the mixture.

$C_8F_{17}CH_2CH_2OCOCR^1=CH_2$ is used as a fluorine-containing monomer for producing a polymer. The polymer obtained by polymerization of this monomer is useful as a water- and oil-repellent.

In order to achieve the first object, in the first aspect, the present invention provides a method for producing a mixture of fluoroalkyl iodide telomers by telomerization, each of which telomers is represented by the formula (I):

$$R_f(CF_2CF_2)_nI \quad (I)$$

wherein $R_f$ represents a fluoroalkyl group having 1 to 10 carbon atoms and n is an integer representing a polymerization degree, with the polymerization degree n equal to or more than k that is an integer of 3 or more, which includes the steps of:

(1) obtaining a first reaction mixture containing a mixture of fluoroalkyl iodide telomers represented by the formula (I) with the polymerization degree n of 1 or more by reacting tetrafluoroethylene with a fluoroalkyl iodide of the formula: $R_fI$ wherein $R_f$ represents a fluoroalkyl group having 1 to 10 carbon atoms in a first reactor;

(2) separating the first reaction mixture into:
   a first fraction including a fluoroalkyl iodide telomer of the formula (I) with the polymerization degree n equal to or less than (k−2) or a mixture thereof, and the fluoroalkyl iodide represented by the formula: $R_fI$;
   a second fraction including a fluoroalkyl iodide telomer represented by the formula (I) with the polymerization degree n of (k−1); and
   a third fraction including a mixture of fluoroalkyl iodide telomers each of which is represented by the formula (I) with the polymerization degree n equal to or more than k; and (3) obtaining a second reaction mixture including a mixture of fluoroalkyl iodide telomers each of which is represented by the formula (I) with the polymerization degree n equal to or more than k, by reacting the second fraction with tetrafluoroethylene in a second reactor.

The fluoroalkyl iodide telomer produced according to this method is a compound represented by the formula (I). In the formula (I), $R_f$ represents any one of fluoroalkyl groups 1 to 10 carbon atoms. $R_f$ corresponds to a fluoroalkyl group of a fluoroalkyl iodide that is a starting material of the telomerization.

A "mixture of fluoroalkyl iodide telomers" (fluoroalkyl iodide telomer is merely referred to as "telomer" hereinafter) means a mixture including a plurality of telomers whose polymerization degree n are different from each other.

The object to be produced in accordance with the production method of the present invention is a mixture of fluoroalkyl iodide telomers (fluoroalkyl iodide telomer is merely referred to as "telomer" hereinafter) with the polymerization degree n equal to or more than k. This mixture is a mixture of telomers whose polymerization degrees are k, (k+1), (k+2), . . . , respectively. However, this mixture inevitably contains telomers with the polymerization degree n of less than k and an unreacted fluoroalkyl iodide and so on depending on telomerization conditions and separation conditions for reaction mixtures. The mixture which includes the compounds contained inevitably is included in the object to be produced in accordance with the production method of the present invention.

In this specification, a mixture of telomers with the polymerization degree n equal to or more than p is often indicated as "$\geq R_f(CF_2CF_2)_pI$" using "$\geq$." Further, a mixture of telomers with the polymerization degree n equal to or less than q is often indicated as "$\leq R_f(CF_2CF_2)_pI$" using "$\leq$."

In the production method of the present invention, "k" is one integer selected from integers of 3 and more. Depending on the intended end-usage of the telomer, k is selected desirably. In the mixture of the telomers with n not less than k, a polymerization degree $n_{max}$ of a telomer having the maximum polymerization degree depends on telomerization conditions. Generally, $n_{max}$ is about 20. The mixture obtained according to the production method of the present invention preferably contains a telomer whose polymerization degree n is k in a largest amount.

The present method for producing a mixture of telomers is characterized in that two reactors are used, and a mixture of telomers is obtained by reacting a fluoroalkyl iodide represented by the formula: $R_fI$ (wherein $R_f$ represents any one of fluoroalkyl groups having 1 to 10 carbon atoms) with TFE in a first reactor, followed by separating a telomer whose polymerization degree n is (k−1) from this mixture, and then the telomer is reacted with the TFE in a second reactor. The use of the second reactor makes it possible to increase the ratio of the telomer whose polymerization degree is k in a product (that is, the mixture of the telomers with the polymerization degree n equal to or more than k).

In the production method of the present invention. both of the first and the second reactors are not limited to particular shapes, any reactor employed conventionally for telomerization (for example, an autoclave) can be used. Further, the production method of the present invention can be carried out by a simple operation.

In order to achieve the second object, in the second aspect, the present invention provides a method for producing a mixture of (meth)acrylate esters, each of which is represented by the formula (III):

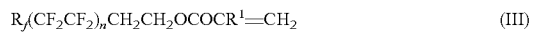
$$R_f(CF_2CF_2)_nCH_2CH_2OCOCR^1\!=\!CH_2 \qquad (III)$$

wherein $R_f$ represents a fluoroalkyl group having 1 to 10 carbon atoms, $R^1$ represents a hydrogen atom or a methyl group, and n is an integer representing a polymerization degree, with the polymerization degree n equal to or more than k that is an integer of 3 or more, which includes:

(A) a telomerization step of producing a mixture of fluoroalkyl iodide telomers represented by the formula (I) with the polymerization degree n equal to or more than k that is an integer of 3 or more, according to the method for producing the mixture of the telomers;

(B) an ethylene addition step of obtaining a mixture of ethylene adducts, each of which is represented by the formula (II):

$$R_f(CF_2CF_2)_nCH_2CH_2I \qquad (II)$$

in which polymerization degree n is equal to or more than k that is an integer of 3 or more, by adding ethylene to the mixture of the fluoroalkyl iodide telomers obtained in the step (A); and (C) an esterification step of obtaining the above mixture of the fluorine-containing (meth)acrylate esters by reacting the mixture of the ethylene adducts obtained in the step (B) with a (meth)acrylate compound.

A "mixture of fluorine-containing (meth)acrylate esters with the polymerization degree n equal to or more than k" means a mixture including a plurality of fluorine-containing (meth)acrylate esters which have k, (K+1), (k+2), . . . , as "n" in the group $R_f(CF_2CF_2)_nCH_2CH_2O$— of the formula (III), respectively. In the present method for producing the mixture of the fluorine-containing (meth)acrylate esters, the mixture of the telomers are produced according to the production method described above, and then ethylene is added to the mixture followed by reacting the resultant adduct with the (meth)acrylic acid compound. Therefore, in the mixture of the esters represented by the formula (III), which is a product, n of each ester that constitutes the mixture is an integer of 3 or more.

The present method for producing the mixture of the fluorine-containing (meth)acrylate esters is characterized in that it includes the step of producing the mixture of the telomers with the polymerization degree n equal to or more than the predetermined value k. This feature makes it possible to produce a mixture of fluorine-containing (meth)acrylate esters in which the number of carbon atoms of the alkoxyl group is not less than a predetermined value, selectively.

In the method for producing the mixture of the fluorine-containing (meth)acrylate esters, the steps (A) and (B) do not necessarily need to be conducted continuously. For example, the method for producing the mixture of the fluorine-containing (meth)acrylate esters may be a method wherein the step (B) is started using as a stating material the mixture of the telomers which is an "end product" obtained according to the above method followed by subjecting the mixture obtained in the step (B) to the step (C). That is, the mixture of the fluorine-containing (meth)acrylate esters each of which is represented by the above formula (III) with the polymerization degree equal to or more than k (k is any one of integers not less than 3) is produced according to a method which includes adding ethylene to the mixture of the fluoroalkyl iodide telomers each of which is represented by the formula (I) with the polymerization degree n equal to or more than k (k is an integer not less than 3), which is produced according to the above-described production method of the first aspect, and reacting the resultant adduct with the (meth)acrylic compound. Also this production method is included in the scope of the present invention.

EMBODIMENT FOR CARRYING OUT THE INVENTION

Figure 1:
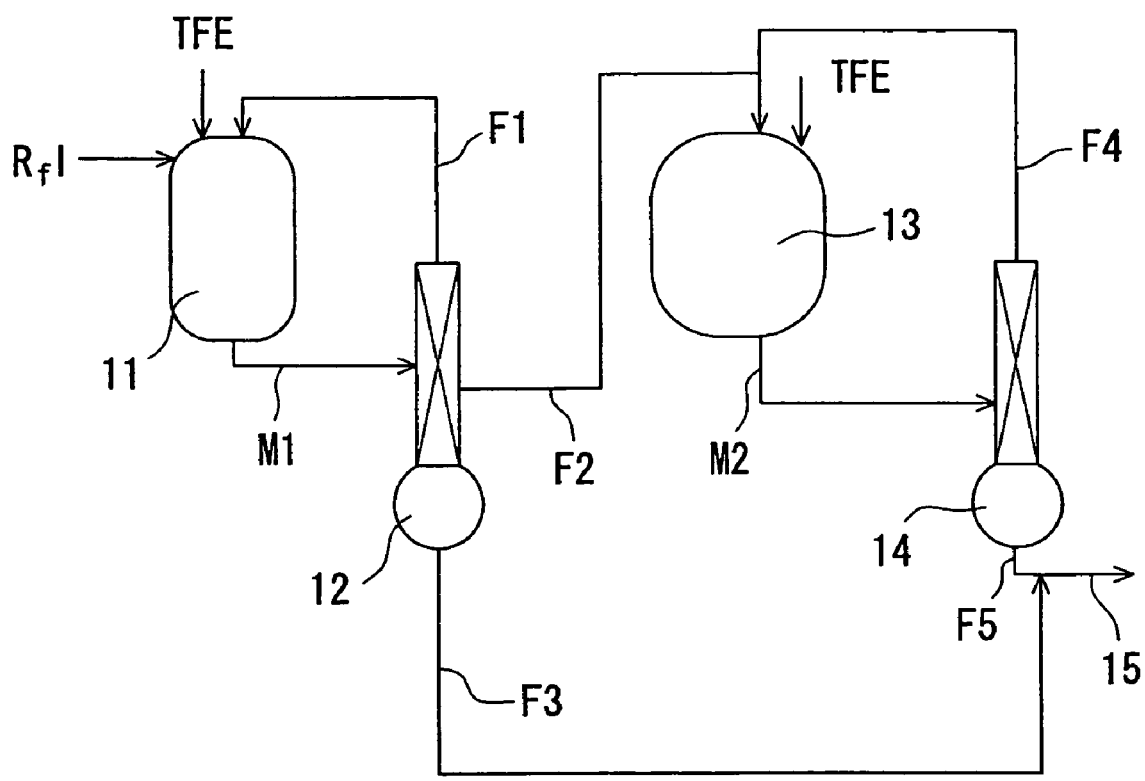
FIG. 1 schematically shows one embodiment of a method for producing a mixture of telomers according to the present invention.

The method for producing a mixture of fluoroalkyl iodide telomers which is the first aspect of the present invention is a method for producing $\geq R_f(CF_2CF_2)_k I$ (wherein $R_f$ represents any one of fluoroalkyl groups having 1 to 10 carbon atoms, and k is an integer equal to or more than 3 which corresponds to the polymerization degree) by means of telomerization, which includes the steps of:

(1) obtaining a first reaction mixture including $\geq R_f(CF_2CF_2)I$ by reacting a fluoroalkyl iodide $R_f I$ with TFE in a first reactor;

(2) separating the first reaction mixture into:
a first fraction including $\leq R_f(CF_2CF_2)_{k-2} I$ and unreacted starting materials;
a second fraction including $R_f(CF_2CF_2)_{k-1} I$; and
a third fraction including $\geq R_f(CF_2CF_2)_k I$; and (3) obtaining a second reaction mixture including $\geq R_f(CF_2CF_2)_k I$ by reacting the second fraction with tetrafluoroethylene in a second reactor.

The steps (1) to (3) are described hereinafter.

The first step (1) is a step wherein telomerization is carried out in the first reactor. The telomerization is carried out by reacting the fluoroalkyl iodide represented by the formula: $R_f I$ with TFE. In $R_f I$, $R_f$ is any one of fluoroalkyl groups having 1 to 10 carbon atoms. $R_f$ is preferably any one of fluoroalkyl groups having 1 to 8 carbon atoms, and more preferably any one of fluoroalkyl groups having 1 to 5 carbon atoms. Further, $R_f$ is preferably a perfluoroalkyl group.

Examples of the fluoroalkyl iodide $R_f I$ include trifluoromethyl iodide, pentafluoroethyl iodide, perfluoroisopropyl iodide, and perfluoro-n-butyl iodide. Of these, pentafluoroethyl iodide ($C_2F_5I$) is generally used for telomerization of TFE. $C_2F_5I$ is preferably used also in the production method of the present invention.

In the step (1), telomerization may be carried out under conditions which are conventionally employed in the production of fluoroalkyl iodide telomer. Specifically, the reaction temperature is set at between 30 and 150° C. and the reaction pressure is set at between 0.01 and 2 MPa for proceeding the reaction. The reaction time is generally in the range of 0.1 to 10 hours. The reaction pressure is a pressure generated by TFE which is forced into the reactor. The specific pressure is a gauge pressure. In this specification including the following description, a pressure is indicated by its gauge pressure unless expressly stated.

Telomerization may be carried out under the presence of catalyst. The catalyst is, for example, an organic peroxide, a transition metal, or $IF_5.SbF_5$. The organic peroxides suitable for the catalyst are, for example, a carboxylate peroxide compound such as t-butylperoxypivalate, peroxymonocarbonate such as t-butyl peroxyisopropyl monocarbonate, and peroxydicarbonate compound such as bis-(4-alkylcyclohexyl)peroxydicarbonate. The catalyst is used in an amount of about 0.001 to 0.1 mol per mole of the fluoroalkyl iodide ($R_f I$).

In the first reactor, molar ratio of the fluoroalkyl iodide ($R_f I$) to tetrafluoroethylene (TFE) is preferably in the range of 20:80 to 99:1. As $R_f I$/TFE is larger (that is, as the molar ratio of TFE is smaller), $n_{max}$ is smaller and an average polymerization degree $n_{ave}$ is smaller in the produced mixture of the telomers. Therefore, it is preferable that $R_f I$/TFE is larger when it is intended that $n_{max}$ is smaller and $n_{ave}$ is smaller in the finally obtained telomer mixture. For example, when $C_2F_5I$ is used as $R_f I$ for producing a mixture of telomers with the polymerization degree n equal to or more than 3, a mixture whose $n_{ave}$ is closer to 3 (for example, about 3.05 to 3.4) can be obtained as a product by carrying out the production method of the present invention with $R_f I$:TFE (molar ratio) in the range of 99:1 to 97:3.

In the first reactor, TFE is charged in a vapor phase of the reactor. In that case, the telomerization proceeds at an interface between the vapor phase and a liquid phase. Alternatively, TFE may be charged into $R_f I$ of the liquid phase so that bubbles are generated.

In the step (1), in addition to $R_f I$, one or more telomers of low polymerization degree which are represented by the formula (I) with the polymerization degree n equal to or less than (k−2) may be fed into the first reactor. The telomer(s) of low polymerization degree is converted to a telomer(s) whose polymerization degree is higher by reacting with tetrafluoroethylene in the first reactor. For example, when a mixture of telomers with the polymerization degree n equal to or more than 3 is produced using $C_2F_5I$ as $R_f I$, $C_4F_9I$ (n=1) can be fed into the first reactor. In this case, since n that is (k−2) or less is only "1", only one type of telomer can be fed. When a mixture of telomers with polymerization degree n equal to or more than 4 is produced using $C_2F_5I$ as $R_f I$, $C_4F_9I$ (n=1) and/or $C_6F_{13}I$ (n=2) may be fed into the first reactor. In this case, since n that is (k−2) or less is 1 and 2, one or two types of telomers can be fed into the first reactor.

The telomer(s) with n of (k−2) or less may be, for example, one(s) which is obtained by separating the first reaction mixture in the below-mentioned step (2). That is, feeding one or more types of telomers with n equal to or less than (k−2) may be carried out by returning a portion of the first reaction mixture.

The telomer(s) with n equal to or less than (k−2) which is fed into the first reactor does not necessarily need to be one which is obtained by telomerization of $R_f I$ with TFE. Any compound obtained by a method other than telomerization may be fed into the first reactor as long as the compound has a structure which is represented by the formula (I) with n equal to or less than (k−2). Although such a compound cannot be called "telomer" exactly, such a compound is called "telomer" for convenience.

Next, the step (2) is described. The step (2) is a step wherein the first reaction mixture containing the mixture of the telomers each of which has a polymerization degree n of one or more is separated into the three fractions which contain the above components respectively. However, each fraction may contain other component(s) (for example, telomer which should be contained in the other fraction) in addition to the above components as long as the other component(s) does not affect adversely the production of the telomer mixture according to the present invention. The other component(s) is inevitably contained depending on the property of an apparatus used for the separation and the operation conditions. Each fraction is described hereinafter.

The first fraction includes a fluoroalkyl iodide telomer of low polymerization degree which is represented by the formula (I) with the polymerization degree n equal to or less than (k−2) or a mixture thereof, and an unreacted fluoroalkyl iodide represented by the formula: $R_fI$. The first fraction sometimes contains unreacted TFE in the form of a vapor phase and/or a liquid phase. The first fraction is preferably returned to the first reactor from the viewpoint of production efficiency.

In the above, "a fluoroalkyl iodide telomer with the polymerization degree n equal to or less than (k−2) or a mixture thereof" means that, depending on the value of k, the number of types of the telomers whose n is (k−2) or less becomes only one or more than one. For example, in the case of k=3, the telomer with n of (k−2) or less is only the telomer whose n is 1 (that is, one type), and does not become a mixture. In the case of k=4, the telomer with n of (k−2) or less becomes a mixture of two types of telomers whose n are 1 and 2 respectively.

The first fraction may contain other component(s) in addition to the telomers whose polymerization degree n is (k−2) or less, RfI, and TFE. The other component is, for example, telomer(s) with the polymerization degree n of more than (k−2). As described above, the other component may be inevitably contained in the first fraction depending on the property of the separation apparatus and so on. It is preferable that the amount of the other component(s) contained in the first fraction is as small as possible (for example, 0.1 mol % or less).

The second fraction contains a fluoroalkyl iodide telomer which is represented by the formula (I) with n of (k−1). The second fraction is subjected to the telomerization in the below-mentioned step (3). The second fraction may contain other component(s) such as a telomer whose polymerization degree is less or more than (k−1), in addition to the telomer whose polymerization degree n is (k−1). As described above, the other component may be inevitably contained in the second fraction depending on the property of the separation apparatus and so on. It is preferable that the amount of the other component(s) contained in the second fraction is as small as possible (for example, 0.1 mol % or less).

The third fraction contains a mixture of fluoroalkyl iodide telomers each of which is represented by the formula (I) with the polymerization degree n of k or more. The third fraction is withdrawn as the intended product. The third fraction may contain other component(s) such as a telomer whose polymerization degree n is (k−1) or less, in addition to the telomers with the polymerization degree n of k or more. As described above, the other component(s) may be inevitably contained in the third fraction depending on the property of the separation apparatus and so on. It is preferable that the amount of the other component(s) contained in the third fraction is as small as possible (for example, 0.1 mol % or less).

In the step (2), each fraction may be separated simultaneously in a single apparatus for separation. Alternatively, the step (2) may be carried out in two stages. That is, the step (2) may be carried out by separating the first reaction mixture into the first fraction and an intermediate fraction including the second fraction and the third fraction followed by separating the intermediate fraction into the second fraction and the third fraction in another apparatus for separation.

The step (2) is preferably carried out using a distillation column. The distillation column may be any one of a plate column and a packed column. When the step (2) is carried out by continues distillation in a single distillation column, the first fraction is withdrawn continuously from the top of the column, the third fraction is withdrawn continuously from the bottom of the column and the second fraction is withdrawn continuously from the middle position of the column as a side-cut. Alternatively, the step (2) may be a batch distillation using a single distillation column. In that case, the first fraction and the second fraction are obtained as distillates by being distilled off in this order. The third fraction is obtained as a still residue or a distillate which is distilled off after the first and the second fractions have been distilled off.

In the case where the step (2) is carried out in two stages using two distillation columns, the first fraction is withdrawn from the top of the first distillation column, and the intermediate fraction is withdrawn from the bottom of the first distillation column. The intermediate column is passed to the second distillation column and subjected to distillation. The second fraction is withdrawn from the top of the second distillation column, and the third fraction is withdrawn from the bottom of the second distillation column. Each distillation carried out in each of the first and the second distillation columns may be continuous distillation or batch distillation.

The step (2) may be carried out by any method other than distillation. For example, the step (2) may be carried out by extraction or membrane separation.

Next, the step (3) is described. The step (3) is a step of reacting the telomer having the polymerization degree n of (k−1) that is contained in the second fraction obtained in the step (2) with TFE in the second reactor. The step (3) is a step of obtaining a mixture of telomers with the polymerization degree n of k or more by telomerizing the low-polymerization-degree telomer whose n is smaller than k by one. The step (3) is carried out in the same manner as the step (1) by feeding the telomer having n of (k−1) and TFE into the second reactor. Therefore, the detailed description as to the conditions of the step (3) is omitted. The preferable molar ratio of the telomer to TFE in the first reactor is the same as the preferable molar ratio of $R_fI$ to TFE described concerning the step (1).

The second reaction mixture obtained in the step (3) usually contains the unreacted telomer having n of (k−1) in addition to the intended mixture of telomers with n equal to or more than k. Therefore, the second reaction mixture is preferably separated into a fourth fraction which contains the fluoroalkyl iodide telomer which is represented by the formula (I) with the polymerization degree n of (k−1) and a fifth fraction which contains a mixture of fluoroalkyl iodide telomers each of which is represented by the formula (I) with the polymerization degree n of k or more. The fourth fraction is preferably returned to the second reactor. The fifth fraction is withdrawn as a product. The fifth fraction may be withdrawn together with the third fraction separated in the step (2) via a single line.

The separation of the second reaction mixture is preferably carried out using a distillation column. In that case, the fourth fraction is withdrawn from the top of the column, and the fifth fraction is withdrawn from the bottom of the column. The distillation may be batch distillation or continuous distillation. Alternatively, this separation may be carried out by extraction or membrane separation.

When the first reaction mixture obtained in the first reactor is fractionated in two stages using the first and the second distillation columns as described above, a distillation column for separating the second reaction mixture may serve as the second distillation column. In that case, the intermediate fraction from the first reaction mixture and the second reaction mixture may be passed to the second distillation column via a single line. Further, in that case, the second fraction from the first reaction mixture and the fourth fraction from the second reaction mixture are withdrawn together from the top of the second distillation column, and the third fraction from the first reaction mixture and the fifth fraction from the second reaction mixture are withdrawn together from the bottom of the column.

By carrying out each step described above, a mixture of telomers with the polymerization degree n equal to or more than k can be produced preferably in a manner such that the ratio of the telomer having n of k is large. This telomer mixture is useful as a material for various chemical products, and particularly suitable for producing a fluorine-containing acrylate ester. Hereinafter, a method for producing a mixture of fluorine-containing acrylate esters, which is the second aspect of the present invention, is described.

As described above, a method for producing a fluorine-containing acrylate esters of the second aspect of the present invention is a method for producing a mixture of fluorine-containing (meth)acrylic esters, each of which is represented by the formula (III):

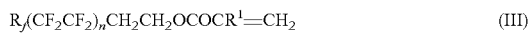

wherein $R_f$ represents a fluoroalkyl group having 1 to 10 carbon atoms, $R^1$ represents a hydrogen atom or a methyl group, n is an integer representing a polymerization degree, having the polymerization degree n equal to or more than k that is an integer of 3 or more, which includes:

(A) a telomerization step of obtaining the mixture of the fluoroalkyl iodide telomers in accordance with the above-described method of the present invention for producing the mixture of the telomers;

(B) an ethylene addition step of obtaining a mixture of ethylene adducts by adding ethylene to the mixture of the fluoroalkyl iodide telomers obtained in the step (A); and (C) an esterification step of obtaining the intended mixture of the fluorine-containing (meth)acrylic esters by reacting the mixture of the ethylene adducts obtained in the step (B) with a (meth)acrylic compound.

Hereinafter the steps (A) to (C) are described.

The step (A) may be carried out in the same manner as the method for producing the telomer mixture which is described above. Therefore, the detailed description as to the step (A) is omitted here.

The step (B) is a step of adding ethylene to the mixture of the telomers obtained in the step (A). The step (B) may be carried out under the conditions conventionally employed in an ethylene addition reaction. Specifically, ethylene addition is carried out by setting the reaction temperature at between 30 and 250° C., for example between 50 and 220° C., and setting the reaction pressure at 1 MPa or less, for example between 0.2 and 0.4 MPa. The reaction time is generally in the range of 0.1 to 10 hours. The reaction pressure is a pressure generated by ethylene which is forced into the reactor. The reaction is preferably carried out by setting the molar ratio of the telomer mixture to ethylene at between 1:2 and 1:0.05.

The ethylene addition reaction may be carried out under the presence of a catalyst which generates free radical. For example, the catalyst is an azo compound or an organic peroxide. The azo compound suitable for the catalyst is, for example α,α'-azobisisobutyronitrile. The organic peroxide suitable for the catalyst is, for example, a diacyl peroxide such as benzoyl peroxide, a dialkyl peroxide such as t-butyl peroxide, or a peroxymonocarbonate such as t-butyl peroxyisopropyl monocarbonate. The catalyst is used in an amount of 0.005 to 0.2 mol per mole of the telomer mixture.

As a result of the step (B), a mixture of the ethylene adducts represented by the above formula (II) is obtained. The polymerization degree n of —(CF$_2$CF$_2$)— in each ethylene adduct contained in the mixture depends on the polymerization degree n in the telomer obtained in the step (A). Since the mixture of the telomers having n of k or more is obtained in the step (A), the mixture of the ethylene adducts obtained in the step (B) also becomes a mixture of the ethylene adducts having n of k or more. The mixture of the ethylene adducts is esterified in the next step (C).

The step (C) is a step of obtaining the intended mixture of the fluorine-containing (meth)acrylate esters by reacting the mixture of the ethylene adducts obtained in the step (B) with a (meth)acrylic compound. The (meth)acrylic compound is, for example a metal salt of a (meth)acrylic acid. The metal salt of the (meth)acrylic acid is, for example a salt of alkali metal such as potassium or sodium, or a salt of alkaline-earth metal. The step (C) may be carried out under the conditions conventionally employed in an esterification reaction. Specifically, the reaction is carried out by setting the reaction temperature at between 160 and 220°C., for example between 170 and 190° C. The reaction time is generally in range of 0.1 to 10 hours.

By conducting each of the above-described steps, the intended mixture of the fluorine-containing (meth)acrylate esters is obtained. In this ester mixture, the polymerization degree of —(CF$_2$CF$_2$)— in each ester is k or more. This is because the polymerization degree n in each telomer is k or more in the telomer mixture obtained in the step (A). Therefore, it is possible to obtain a mixture of esters wherein the number of carbon atoms of the alkoxyl group in each ester (corresponding to R$_f$(CF$_2$CF$_2$)$_n$CH$_2$CH$_2$O- in the formula (III)) is equal to or more than a desired value by producing the telomers setting k at the desired value.

As described above, a telomer mixture wherein the maximum polymerization degree $n_{max}$ is small and the average polymerization degree $n_{ave}$ is closer to k can be obtained by carrying out the telomerization in two reactors preferably in a manner such that the molar ratio of R$_f$I to TFE is larger. Therefore, it is possible to obtain a desired ester more selectively by setting k depending on the desired ester and producing the ester in accordance with the production method of the present invention.

When the mixture of the fluorine-containing (meth)acrylate esters is produced according to the production method of the present invention, a mixture of olefins represented by R$_f$(CF$_2$CF$_2$)$_n$CH$_2$CH$_2$CH=CH$_2$ is synthesized as a by-product. This olefin mixture is impurity, and therefore it is preferable that the ratio of this olefin mixture in the ester mixture is smaller. However, since this olefin has a boiling point depending on the value of n, which is sometimes close to a boiling point of the ester, this olefin is sometimes difficult to be removed from the ester mixture even by rectification. For example, when an ester mixture wherein R$_f$ is C$_2$F$_5$ and n is 3 or more, it is difficult to remove high-molecular-weight olefins with n of 5 or more, of the by-product olefins.

The value of n in the by-product olefin depends on the polymerization degree in the telomer obtained in the step (A). As described above, since the telomer mixture wherein $n_{max}$ is small and $n_{ave}$ is close to k is obtained according to the production method of the present invention, also the olefin mixture which is obtained as the by-product upon producing the ester mixture using the telomer mixture becomes one wherein $n_{max}$ is small and $n_{ave}$ is close to k. Therefore, according to the method of the present invention, it is possible to obtain an ester mixture wherein the content of the high-molecular-weight olefins which are difficult to be removed is small, which results in significant improvement of the quality of the product.

The mixture of the fluorine-containing acrylate esters can be used as a monomer for producing a polymer. The polymer produced using these esters is used as a water- and oil-repellent.

Particularly, a polymer produced using $C_8F_{17}CH_2CH_2OCOCR^1=CH_2$ which is an ester wherein $R_f$ is $C_2F_5$ and n is 3 is useful as a water- and oil-repellent. A mixture wherein the content of this ester is large can be obtained by producing the telomer mixture in accordance with the production method of the present invention selecting 3 as k and using $C_2F_5I$ as the fluoroalkyl iodide $R_fI$, followed by subjecting the obtained telomers to an ethylene addition step and a subsequent esterification step.

FIG. 1 schematically shows an embodiment of a method for producing a mixture of telomers of the present invention.

FIG. 1 show a process for producing a mixture of fluoroalkyl iodide telomers with polymerization degree n equal to or more than 3 using $C_2F_5I$ as a fluoroalkyl iodide $R_fI$. In FIG. 1, a reference numeral 11 indicates a first reactor, a reference numeral 12 indicates a first distillation column, a reference numeral 13 indicates a second reactor, a reference numeral 14 indicates a second distillation column. FIG. 1 shows the present invention schematically, and does not show a process of condensing a fraction from the top of each distillation column by means of a condenser and refluxing a portion of condensate to the distillation column.

In the first reactor 11, fresh $C_2F_5I$ and TFE are charged. In the first reactor 11, TFE is telomerized by $C_2F_5I$ resulting in a production of a mixture of telomers represented by the following formula (I):

$$R_f(CF_2CF_2)_nI \tag{1}$$

having a polymerization degree n equal to or more than 1. A first reaction mixture M1 containing the mixture of the telomers and unreacted $C_2F_5I$ and TFE is withdrawn from the first reactor 11 and passed to the first distillation column 12 where the reaction mixture is fractionated by distillation. From the top of the first distillation column 12, a first fraction F1 containing unreacted $C_2F_5I$ and TFE, and $C_4F_9I$ which is a telomer with the polymerization degree n of 1 is withdrawn. From the middle position of the first distillation column 12, a second fraction F2 containing $C_6F_{13}I$ which is a telomer with the polymerization degree n of 2 is withdrawn as a side-cut. From the bottom of the first distillation column 12, a third fraction F3 which contains a mixture of telomers having n equal to or more than 3 (that is, $\geq C_8F_{17}I$) is withdrawn. In the embodiment shown in FIG. 1, the first fraction F1 is recycled to the first reactor 11.

The second fraction F2 is fed into the second reactor 13. The second fraction F2 reacts with TFE which is fed into the second reactor 13, resulting in a production of a second reaction mixture M2 containing telomers whose polymerization degrees are increased by 1 or more, that is, $\geq C_8F_{17}I$.

In the illustrated embodiment, the second reaction mixture M2 obtained in the second reactor 13 is passed to the second distillation column 14 where the reaction mixture is fractionated by distillation. From the top of the second distillation column 14, a fourth fraction F4 containing a telomer $C_6F_{13}I$ whose polymerization degree n is 2 is withdrawn. From the bottom of the second distillation column 14, a fifth fraction F5 containing a mixture of telomers each of which has the polymerization degree n of 3 or more (that is, $\geq C_8F_{17}I$) is withdrawn. In the illustrated embodiment, the fourth fraction F4 is recycled to the second reactor 13.

The third fraction F3 withdrawn from the first distillation column 12 and the fifth fraction F5 withdrawn from the second distillation column 14 are finally withdrawn as a product from a single line 15. The line 15 from which the product is withdrawn may be connected to another production line for producing another product whose material is the product withdrawn from the line 15. For example, when the mixture of the telomers is used for producing a mixture of fluorine-containing (meth)acrylate esters, the line 15 may be connected to a reactor wherein ethylene is added to the telomer mixture. In that case, the illustrated process corresponds to the step of telomerization which is included in the above-described method for producing a mixture of fluorine-containing (meth)acrylate esters of the present invention.

Figure 2:
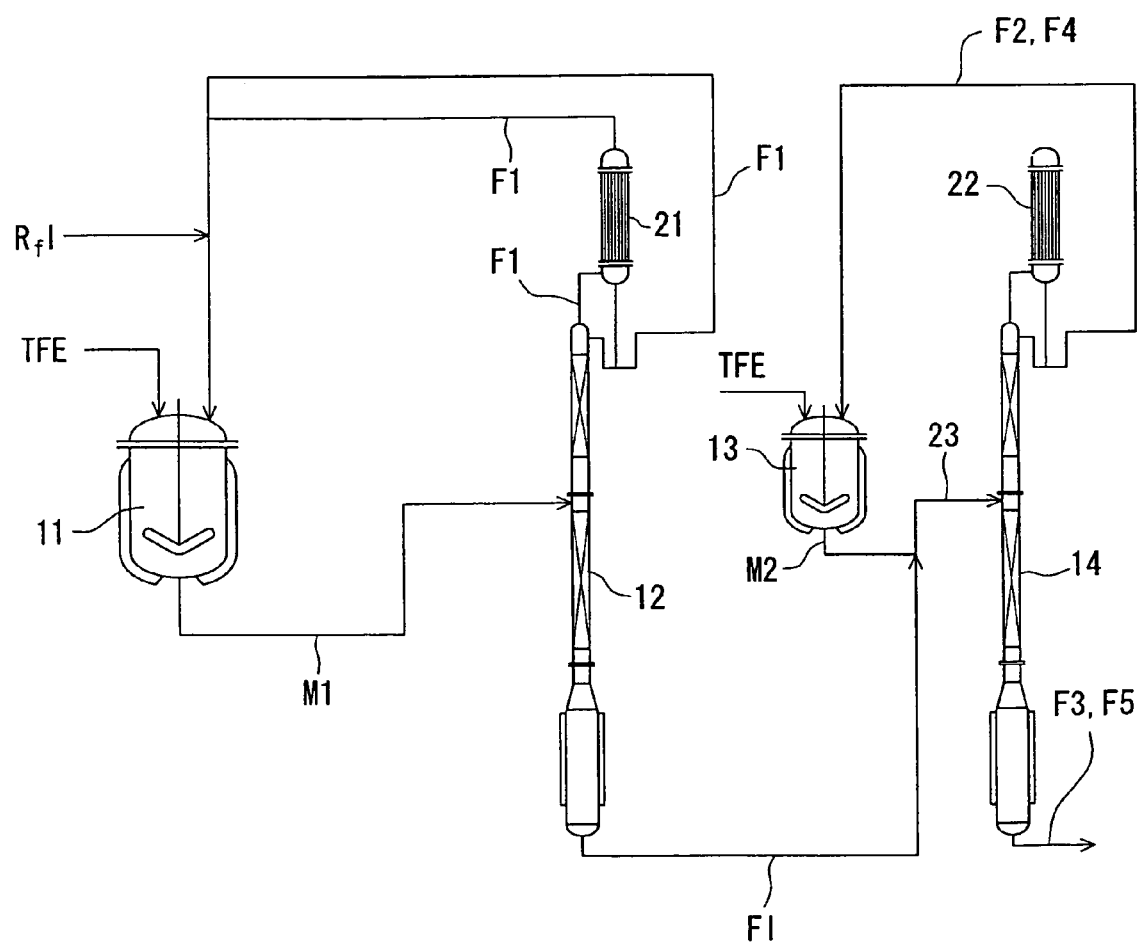
FIG. 2 schematically shows another embodiment of a method for producing a mixture of telomers according to the present invention.

FIG. 2 schematically shows another embodiment of the method for producing the telomer mixture of the present invention. Also in the embodiment shown in FIG. 2, $C_2F_5I$ is used as a fluoroalkyl iodide $R_fI$ and a mixture of the fluoroalkyl iodide telomers with n equal to or more than 3 is produced. In FIG. 2, the numerals used in FIG. 1 denote identical components as those in FIG. 1.

In FIG. 2, a first condenser 21 and a second condenser 22 which condense fractions from the first distillation column 12 and the second distillation column 14 respectively are shown. The first distillation column 12 separate the first reaction mixture M1 into the first fraction F1, an intermediate fraction FI containing the second fraction F2 and the third fraction F3. The first fraction F1 withdrawn from the top of the first distillation column 12 is condensed in the first condenser 21. A portion of the condensed first fraction F1 is refluxed to the first distillation column 12 and the remaining is recycled to the first reactor 11. Also the first fraction F1 which is not condensed in the first condenser 21 is recycled from the top of the first condenser 21 to the first reactor 11.

The intermediate fraction FI is passed to the second distillation column 14 and separated into the first fraction F2 and the third fraction F3. The second distillation column 14 also separates the second reaction mixture M2 obtained in the second reactor 13 into the fourth fraction F4 and the fifth fraction F5. In the illustrated embodiment, the intermediate fraction FI and the second reaction mixture M2 conflow so as to be passed to the second distillation column 14 via a single line 23. Therefore, the second fraction F2 and the fourth fraction F4 are distilled off from the top of the second distillation column 14, and the third fraction F3 and the fifth fraction F5 are withdrawn together from the bottom of the distillation column 14. The fraction from the top of the second distillation column 14 is condensed in the second condenser 22. A portion of condensate is refluxed to the second distillation column 14 and the remaining is recycled to the second reactor 13.

FIGS. 1 and 2 are the schematic views illustrating the method of the present invention. The processes shown in FIGS. 1 and 2 may include using other elements or apparatus employed conventionally in telomerization and distillation. For example, the processes shown in FIGS. 1 and 2 contain evaporating a portion of the fractions withdrawn from the bottoms of the distillation columns 12 and 14 by means of a reboiler and returning it to the bottoms.

The present application claims a priority under the Paris Convention to Japanese Patent Application No. 2001-30848 filed on Feb. 7, 2001, entitled "Production of a fluorine-containing monomer. The contents of this application are incorporated herein by the reference thereto in their entirety.

INDUSTRIAL APPLICABILITY

According to a method for producing a mixture of telomers of the present invention, a mixture of the telomers with n equal to or more than k (k is an integer of 3 or more) whose $n_{ave}$ is closer to k. This telomer mixture is useful as a material for producing a compound which has the number of carbon atoms or a molecular weight which is equal to or more than a predetermined value. Specifically, this telomer mixture is preferably used for producing a mixture of fluorine-containing (meth)acrylate esters wherein the number of carbon atoms of an alkoxyl group is equal to or more than a particular value. This mixture of the fluorine-containing (meth)acrylate esters is used as a monomer for producing a polymer. Particularly, a mixture of fluorine-containing (meth)acrylate esters obtained from a mixture of telomers which is represented by $C_{2F5}(CF_2CF_2)_nI$ with the polymerization degree n equal to or more than 3 is preferably used as a monomer for producing a polymer that is useful as a water- and oil-repellent.

EXAMPLES

Hereinafter the present invention is specifically described by examples.

Example 1

Production of a Mixture of Fluoroalkyl Iodide Telomers

A mixture of telomers represented by $C_2F_5(CF_2CF_2)_nI$ with the polymerization degree n equal to or more than 3 was continuously produced by means of an apparatus as shown in FIG. 1. In this example, a 500 mL autoclave with a stirrer was employed as a first reactor 11 and a 200 mL autoclave with a stirrer was employed as a second reactor 13.

Into the first reactor 11, 430 g (1.75 mol) of $C_2F_5I$ as a fluoroalkyl iodide $R_fI$, 200 g (0.578 mol) of $C_4F_9I$ as a telomer of n=1, and 0.063 g of tert-butyl peroxyisopropyl monocarbonate as a catalyst were charged and heated to 115° C. being stirred. The heated mixture was reacted with tetrafluoroethylene by charging TFE into a vapor phase continuously so as to maintain the reaction pressure at 1.2 MPa, resulting in a production of a first reaction mixture M1. The first reaction mixture M1 in a form of a liquid phase was continuously withdrawn from the first reactor 11 at a rate of 200 mL per hour.

The withdrawn first reaction mixture was passed to the first distillation column 12 where the mixture was separated into three fractions by continuous distillation. The first distillation column 12 was a packed column having an inner diameter of 20 mm, a packing height of 1200 mm and a theoretical plate number of 25 and having packed therein Dixon packings (1.5 mm). The separation was carried out by supplying the first reaction mixture M1 to the position of the eighteenth plate from the bottom, and continuously withdrawing the first fraction from the top, the second fraction from the middle position (the sixth plate from the bottom) and the third fraction from the bottom under conditions wherein the pressure of the top of first distillation column 12 was 0.15 MPa and reflux ratio was 2.0. The components contained in each of the first to the third fractions are shown in the following:

| The first fraction F1: | tetrafluoroethylene, $C_2F_5I$ and $C_4F_9I$; |
|---|---|
| The second fraction F2: | $C_6F_{13}I$; |
| The third fraction F3: | $\geq C_8F_{17}I$ |

After separation, the first fraction F1 was recycled to the first reactor 11. The second fraction F2 was passed to the second reactor 13. The third fraction 13 was withdrawn as a product.

During withdrawing the first reaction mixture M1 from the first reactor 11 continuously, telomerization was conducted continuously by additionally charging $C_2F_5I$ in an amount that was equal to the number of mole of the telomers which were withdrawn out of the system as the second fraction F2 and the third fraction F3, and tert-butyl peroxyisopropyl monocarbonate in an amount of 0.04 g per hour into the first reactor 11, with the reaction pressure constant.

The telomerization was continuously conducted until the composition of the telomers contained in the first reaction mixture M1 withdrawn out of the first reactor 11 was constant, so that $C_6F_{13}I$ having polymerization degree n of 2 was withdrawn from the first reactor 11 in a constant amount per hour. The composition of telomers contained in the first reaction mixture M1 withdrawn per hour became constant as follows:

| The first fraction F1: | $C_2F_5I$ | 267.2 g (1.09 mol) |
|---|---|---|
| | $C_4F_9I$ | 124.3 g (0.36 mol) |
| The second fraction F2: | $C_6F_{13}I$ | 21.3 g (0.05 mol) |
| The third fraction F3 | $C_8F_{17}I$ | 5.3 g (0.01 mol) |
| | $C_{10}F_{21}I$ | 1.4 g (0.002 mol) |
| | $\geq C_{12}F_{25}I$ | 0.1 g. |

Next, 345 g (0.77 mole) of $C_6F_{13}I$ which was the second fraction F2 separated from the first reaction mixture M1 and 0.0289 of tert-butyl peroxyisopropyl monocarbonate as a catalyst were charged into the second reactor 13, and heated to 115° C. being stirred. The heated mixture was reacted with tetrafluoroethylene by charging TFE into a vapor phase so as to maintain the reaction pressure at 0.13 MPa, resulting in a production of a second reaction mixture M2. The second reaction mixture M2 in a form of a liquid phase was continuously withdrawn from the second reactor 13 at a rate of 170 mL per hour.

The withdrawn second reaction mixture M2 was passed to the second distillation column 14 where the mixture was separated into two fractions by continuous distillation. The second distillation column 14 was a packed column having an inner diameter of 15 mm, a packing height of 800 mm and a theoretical plate number of 20 and having packed therein Dixon packings (1.5 mm). The separation was carried out by supplying the second reaction mixture M2 to the position of the eleventh plate from the bottom, and continuously withdrawing the fourth fraction from the top and the fifth fraction from the bottom under conditions wherein the pressure of the top of the second distillation column 14 was −0.09 MPa and reflux ratio was 3.0. The components contained in each of the fourth and the fifth fractions are shown in the following:

| The fourth fraction F4: | tetrafluoroethylene and $C_6F_{13}I$; |
|---|---|
| The fifth fraction F5: | $\geq C_8F_{17}I$ |

After separation, the fourth fraction F4 was recycled to the second reactor 13. The fifth fraction F5 was withdrawn as a product. As shown in FIG. 1, the fifth fraction F5 was withdrawn together with the third fraction F3 from the first reaction mixture M1 via a single line 15.

During withdrawing the second reaction mixture M2 from the second reactor 13 continuously, telomerization was conducted continuously by additionally charging $C_6F_{13}I$ in an amount that was equal to the number of mole of the telomers which were withdrawn out of the system as the fifth fraction F5, and tert-butyl peroxyisopropyl monocarbonate in an amount of 0.03 g per hour, with the reaction pressure constant. The additional charging of $C_6F_{13}I$ was carried out by supplying the second fraction into the second reactor 13.

The telomerization was continuously conducted until the composition of the telomers contained in the second reaction mixture M2 withdrawn out of the second reactor 13 was constant, so that the mixture of the telomers having n equal to or more than 3 (that is, $\geq C_8F_{17}I$) was withdrawn from the second reactor 13 in a constant amount per hour. The composition of telomers contained in the second reaction mixture M2 withdrawn per hour became constant as follows:

| | | |
|---|---|---|
| The fourth fraction F4: | $C_6F_{13}I$ | 318.3 g (0.71 mol) |
| The fifth fraction F5: | $C_8F_{17}I$ | 22.1 g (0.04 mol) |
| | $C_{10}F_{21}I$ | 3.7 g (0.006 mol) |
| | $\geq C_{12}F_{25}I$ | 0.9 g |

In this example, the total composition per hour of the intended $\geq C_8F_{17}I$ from the first and the second reactors was as follows:

| | |
|---|---|
| $C_8F_{17}I$ | 27.4 g (0.05 mol) |
| $C_{10}F_{21}I$ | 5.1 g (0.008 mol) |
| $\geq C_{12}F_{25}I$ | 1.0 g |

Example 2

Production of a Mixture of Fluoroalkyl Iodide Telomers

A mixture of telomers each of which was represented by $C_2F_5(CF_2CF_2)_nI$ with the polymerization degree n equal to or more than 3 was continuously produced by means of an apparatus as shown in FIG. 2. In this example, a 500 mL autoclave with a stirrer was employed as a first reactor 11 and a 200 mL autoclave with a stirrer was employed as a second reactor 13.

Into the first reactor 11, 430 g (1.75 mol) of $C_2F_5I$ as a fluoroalkyl iodide $R_fI$, 200 g (0.578 mol) of $C_4F_9I$ as a telomer of n=1, and 0.063 g of tert-butyl peroxyisopropyl monocarbonate as a catalyst were charged and heated to 115° C. being stirred. The heated mixture was reacted with tetrafluoroethylene by charging TFE into a vapor phase continuously so as to maintain the reaction pressure at 1.2 MPa, resulting in a production of a first reaction mixture M1. The first reaction mixture M1 in a form of a liquid phase was continuously withdrawn from the first reactor 11 at a rate of 200 mL per hour.

The withdrawn first reaction mixture was passed to the first distillation column 12 where the mixture was separated into two fractions. The first distillation column 12 was a packed column having an inner diameter of 20 mm, a packing height of 1000 mm and a theoretical plate number of 20 and having packed therein Dixon packings (1.5 mm). The separation was carried out by supplying the first reaction mixture to the position of the fifteenth plate from the bottom, and continuously withdrawing the first fraction from the top, and the intermediate fraction from the bottom under condition s wherein the pressure of the top of first distillation column 12 was 0.10 MPa and reflux ratio was 2.0. The components contained in each of the first fraction and the intermediate fraction are shown in the following:

| | |
|---|---|
| The first fraction F1: | tetrafluoroethylene, $C_2F_5I$ and $C_4F_9I$; |
| The intermediate fraction FI: | $C_6F_{13}I$. |

After separation, the first fraction F1 was recycled to the first reactor 11. The intermediate fraction FI was passed to the second distillation column 14. The second distillation column 14 was a packed column having an inner diameter of 20 mm, a packing height of 1000 mm and a theoretical plate number of 20 and having packed therein Dixon packings (1.5 mm). The separation was carried out by supplying the intermediate fraction FI to the position of the eleventh plate from the bottom, and continuously withdrawing the second fraction F2 from the top, and the third fraction F3 from the bottom under conditions wherein the pressure of the top of second distillation column 14 was −0.09 MPa and reflux ratio was 0.6.

During withdrawing the first reaction mixture M1 from the first reactor 11 continuously, telomerization was conducted continuously by additionally charging $C_2F_5I$ in an amount that was equal to the number of mole of the telomers which were withdrawn out of the system as the intermediate fraction FI, and tert-butyl peroxyisopropyl monocarbonate in an amount of 0.04 g per hour into the first reactor 11, with the reaction pressure constant.

The telomerization was continuously conducted until the composition of the telomers contained in the first reaction mixture M1 withdrawn out of the first reactor 11 was constant. The composition of telomers contained in the first reaction mixture M1 withdrawn per hour became constant as follows:

| | | |
|---|---|---|
| The first fraction F1: | $C_2F_5I$ | 267.2 g (1.09 mol) |
| | $C_4F_9I$ | 124.3 g (0.36 mol) |
| The Intermediate fraction F1 | | |
| The second fraction F2: | $C_6F_{13}I$ | 21.3 g (0.05 mol) |
| The third fraction F3 | $C_8F_{17}I$ | 5.3 g (0.01 mol) |
| | $C_{10}F_{21}I$ | 1.4 g (0.002 mol) |
| | $\geq C_{12}F_{25}I$ | 0.1 g. |

Next, 345 g (0.77 mole) of $C_6F_{13}I$ which was the second fraction F2 separated from the intermediate fraction FI and 0.028 g of tert-butyl peroxyisopropyl monocarbonate as a catalyst were charged into the second reactor 13, and heated to 115° C. being stirred. The heated mixture was reacted with tetrafluoroethylene by charging TFE into a vapor phase continuously so as to maintain the reaction pressure at 0.13 MPa, resulting in a production of a second reaction mixture M2. The second reaction mixture M2 in a form of a liquid phase was continuously withdrawn from the second reactor 13 at a rate of 170 mL per hour.

The withdrawn second reaction mixture M2 was passed to the second distillation column 14 where the intermediate fraction FI was separated, and separated into two fractions by continuous distillation. The distillation was carried out by feeding the second reaction mixture M2 together with the intermediate fraction FI to the second distillation column 14 via a line 23. As a result, from the top of the second distillation column 14, the second fraction from the intermediate fraction FI and the fourth fraction F4 from the second reaction mixture M2 were withdrawn together, and from the bottom of the column, the third fraction F3 from the intermediate fraction FI and the fifth fraction F5 from the second reaction mixture M2 were withdrawn together. The components contained in the fractions withdrawn from the top and the bottom of the second distillation column 14 were as follow:

The fraction from the column top (F2, F4):
tetrafluoroethylene, and $C_6F_{13}I$ The fraction from the column bottom (F3, F5): $\geq C_8F_{17}I$ After separation, the fraction (F2, F4) withdrawn from the top of the second distillation column 14 was recycled to the second reactor 13. The fraction (F3, F5) withdrawn from the bottom of the second distillation column 14 was taken off as a product.

During withdrawing the second reaction mixture M2 from the second reactor 13 continuously, telomerization was conducted continuously by additionally charging $C_6F_{13}I$ in an amount that was equal to the number of mole of the telomers which were withdrawn out of the system as the fifth fraction F5, and tert-butyl peroxyisopropyl monocarbonate in an amount of 0.03 g per hour into the second reactor 13, with the reaction pressure constant. The number of mole of the telomers withdrawn out of the system as the fifth fraction F5 was determined by subtracting the number of mole of the telomers contained in the third fraction from the fraction withdrawn from the bottom of the second distillation 14. The additional charging of $C_6F_{13}I$ was carried out by supplying the fraction withdrawn from the top of the second distillation column 14 into the second reactor 13.

The telomerization was continuously conducted until the composition of the second reaction mixture M2 withdrawn out of the second reactor 13 was constant. Since the composition of the first reaction mixture M1 was already constant, when the composition of the second reaction mixture M2 was constant, the compositions of the fractions which were withdrawn from the top and the bottom of the second distillation column 14 respectively were also constant. In this example, the composition per hour of the fractions withdrawn from the top and the bottom of the second distillation column 14 became constant as follows:

| The fraction from the column top (F2, F4) | |
|---|---|
| $C_6F_{13}I$ | 339.6 g (0.76 mol) |
| The fraction from the bottom (F3, F5) | |
| $C_8F_{17}I$ | 27.4 g (0.05 mol) |
| $C_{10}F_{21}I$ | 5.1 g (0.008 mol) |
| $\geq C_{12}F_{25}I$ | 1.0 g |

The composition of the fraction from the bottom corresponds to the total composition per hour of the intended $\geq C_8F_{17}I$ which were obtained in the first and the second reactors.

Example 3

Production of a Mixture of Fluorine-containing Acrylate Esters

A mixture of fluorine-containing acrylate esters each of which was represented by $C_2F_5(CF_2CF_2)_nCH_2CH_2I$ with the polymerization degree n equal to or more than 3 was produced. In this example, the telomer mixture produced in Example 1 was used. Ethylene was added to this telomer mixture followed by reacting the resultant adduct with an acrylic compound, whereby the intended product was obtained.

Ethylene addition was conducted according to the following procedures. Firstly, 340 g (0.6 mol) of $\geq C_8F_{17}I$ obtained in Example 1 and 0.45 g of tert-butyl peroxyisopropyl monocarbonate were charged into a 200 mL autoclave and heated to 110° C. The heated telomer mixture was reacted with ethylene for 6 hours by charging 17 g (0.6 mol) of an ethylene gas into a vapor phase so that the reaction pressure was maintained at 0.2 MPa. As a result, 358 g (0.6 mol) of a mixture of an ethylene adducts represented by $C_2F_5(CF_2CF_2)_nCH_2CH_2I$ with n equal to or more than 3 was obtained.

Next, an esterification step was conducted according to the following procedures. Firstly, 358 g (0.6 mol) of the mixture of the ethylene adducts obtained in the above-described ethylene addition step was charged into a 500 mL autoclave followed by adding 64 g (0.636 mol) of potassium acrylate and 200 mL of tert-butyl alcohol. The mixture was reacted by being heated up to 180 to 190° C. for 6 hours. After the reaction, the reaction mixture was cooled. Then KI as a byproduct was removed by filtration. The filtrate was distilled in order to remove tert-butyl alcohol, whereby 269 g (0.51 mol) of a mixture of fluorine-containing acrylate esters each of which was represented by the formula: $C_2F_5(CF_2CF_2)_nCH_2CH_2OCOCH=CH_2$ with n equal to or more than 3 was obtained as the intended product.

In the mixture of the fluorine-containing acrylate esters obtained in this example, the content of olefins each of which was represented by $C_2F_5(CF_2CF_2)_nCH_2CH_2CH=CH_2$ with n equal to or more than 5 was less than 0.2 mol %. This means that the method of the present invention makes it possible to produce a mixture of the esters having n equal to or more than 3 wherein the olefin impurity content is low and especially the purity of the ester of n=3 is high. Since the ester of n=3 is a monomer suitable for producing a polymer for a water- and oil-repellent, the resultant mixture is useful as a material for the water- and oil-repellent.

The invention claimed is:

1. A method of producing a mixture of fluorine-containing (meth)acrylate esters, each of which is represented by the formula (III):

$$R_f(CF_2CF_2)_nCH_2CH_2OCOCR^1=CH_2 \quad (III)$$

wherein $R_f$ represents a fluoroalkyl group whose number of carbon atoms is in the range of 1 to 10, $R^1$ represents a hydrogen atom or a methyl group, and n is an integer representing polymerization degree, with the polymerization degree n greater than or equal to k that is an integer of 3 or more, which comprises:

(A) a telomerization step of obtaining the mixture of the fluoroalkyl iodide telomers represented by the formula (I) with the polymerization degree n greater than or equal to k that is an integer of 3 or more, comprising the steps of:

(1) obtaining a first reaction mixture containing a mixture of fluoroalkyl iodide telomers represented by the formula (I):

$$R_f(CF_2CF_2)_nI \quad (I)$$

wherein $R_f$ represents a fluoroalkyl group whose number of carbon atoms is in the range of 1 to 10 and with the polymerization degree n of 1 or more by reacting with tetrafluoroethylene a fluoroalkyl iodide represented by the formula: $R_fI$ wherein $R_f$ represents a fluoroalkyl group whose number of carbon atoms is in the range of 1 to 10 in a first reactor;

(2) separating the first reaction mixture into:

a first fraction including a fluoroalkyl iodide telomer of the formula (I) with the polymerization degree n less than or equal to (k−2) or a mixture thereof, and the fluoroalkyl iodide represented by the formula: $R_fI$;

a second fraction including a fluoroalkyl iodide telomer represented by the formula (I) with the polymerization degree n of (k−1); and a third fraction including a mixture of fluoroalkyl iodide telomers each of which is represented by the formula (I) with the polymerization degree n greater than or equal to k; and (3) obtaining a second reaction mixture including a mixture of fluoroalkyl iodide telomers each of which is represented by the formula (I) with the polymerization degree n greater than or equal to k, by reacting the second fraction with tetrafluoroethylene in a second reactor;

(B) an ethylene addition step of adding ethylene to the mixture of the fluoroalkyl iodide telomers obtained in the step (A) to give a mixture of ethylene adducts, each of which is represented by the formula (II):

$$R_f(CF_2CF_2)_nCH_2CH_2I \quad (II)$$

in which polymerization degree n is greater than or equal to k that is an integer of 3 or more; and (C) an esterification step of reacting the mixture of the ethylene adducts obtained in the step (B) with a (meth)acrylate compound to obtain fluorine-containing (meth)acrylate esters.

2. The method according to claim 1, wherein a mixture of fluorine-containing (meth)acrylate esters each of which is represented by the formula (III) wherein $R_f$ is $C_2F_5$ is and the polymerization degree n is equal to or more than 3 is produced.

3. A method for producing a mixture of fluorine-containing (meth)acrylate esters, each of which is represented by the formula (III):

$$R_f(CF_2CF_2)_nCH_2CH_2OCOCR^1=CH_2 \quad (III)$$

wherein $R_f$ represents a fluoroalkyl group whose number of carbon atoms is in the range of 1 to 10, $R^1$ represents a hydrogen atom or a methyl group, and n is an integer representing polymerization degree, with the polymerization degree n greater than or equal to k that is an integer of 3 or more, which comprises:

adding ethylene to a mixture of fluoroalkyl iodide telomers of formula (I):

$$R_f(CF_2CF_2)_n \quad (I)$$

wherein $R_f$ represents a fluoroalkyl group whose number of carbon atoms is in the range of 1 to 10 and n is an integer representing a polymerization degree with the polymerization degree n greater than or equal to k that is an integer of 3 or more which has been produced by a method comprising the steps of:

(1) obtaining a first reaction mixture containing a mixture of fluoroalkyl iodide telomers represented by the formula (I):

$$R_f(CF_2CF_2)_nI \quad (I)$$

with the polymerization degree n of 1 or more by reacting with tetrafluoroethylene with fluoroalkyl iodide represented by the formula: $R_fI$ wherein $R_f$ represents a fluoroalkyl group whose number of carbon atoms is in the range of 1 to 10 in a first reactor;

(2) separating the first reaction mixture into:

a first fraction including a fluoroalkyl iodide telomer of the formula (I) with the polymerization degree n equal to or less than (k−2) or a mixture thereof, and the fluoroalkyl iodide represented by the formula: $R_fI$;

a second fraction including a fluoroalkyl iodide telomer represented by the formula (I) with the polymerization degree n of (k−1); and a third fraction including a mixture of fluoroalkyl iodide telomers each of which is represented by the formula (I) with the polymerization degree n greater than or equal to k; and (3) obtaining a second reaction mixture including a mixture of fluoroalkyl iodide telomers each of which is represented by the formula (I) with the polymerization degree n greater than or equal to k, by reacting the second fraction with tetrafluoroethylene in a second reactor, followed by reacting the ethylene adducts obtained by adding ethylene to a mixture of fluoroalkyl iodide telomers of formula (I) with a (meth)acrylic compound.

4. The method according to claim 3, wherein a mixture of fluorine-containing (meth)acrylate esters each of which is represented by the formula (III) wherein $R_f$ is $C_2F_5$ and the polymerization degree n is greater than or equal to 3 is produced.

* * * * *